(12) United States Patent
Lee et al.

(10) Patent No.: US 8,268,295 B2
(45) Date of Patent: Sep. 18, 2012

(54) **COSMETIC COMPOSITION FOR SKIN WHITENING COMPRISING THE EXTRACT OF *MAGNOLIA SIEBOLDII* AS ACTIVE INGREDIENT**

(75) Inventors: Ghang Tai Lee, Cheonan-si (KR); Jung Noh Lee, Yeonki-kun (KR); Song Yi Lee, Suwon-si (KR); Seung Ji Lee, Cheonan-si (KR); Kun Kook Lee, Seoul (KR)

(73) Assignee: Coreana Cosmetics Co., Ltd. (KR)

( * ) Notice: Subject to any disclaimer, the term of this patent is extended or adjusted under 35 U.S.C. 154(b) by 0 days.

(21) Appl. No.: 13/462,287

(22) Filed: May 2, 2012

(65) Prior Publication Data
US 2012/0213875 A1  Aug. 23, 2012

Related U.S. Application Data

(62) Division of application No. 12/602,003, filed on Nov. 25, 2009, now abandoned.

(51) Int. Cl.
*A61K 8/00* (2006.01)
(52) U.S. Cl. .......................................... 424/62
(58) Field of Classification Search .................. None
See application file for complete search history.

(56) References Cited

U.S. PATENT DOCUMENTS

| | | | |
|---|---|---|---|
| 5,872,254 A | 2/1999 | Kim et al. | |
| 2003/0198610 A1 | 10/2003 | Nakayama et al. | |

FOREIGN PATENT DOCUMENTS

| | | |
|---|---|---|
| CN | 1493271 | 5/2004 |
| JP | 56-007710 | 1/1981 |
| JP | 4-9315 | 1/1992 |
| JP | 4-9320 | 1/1992 |
| JP | 6-192062 | 7/1994 |
| JP | 9-77635 | 3/1997 |
| JP | 2005-126368 | 5/2005 |
| KR | 10-1998-25843 | 5/1999 |

OTHER PUBLICATIONS

Min-Kyun Na et al., "Inhibitory Activity of Medicinal Plant Extracts against Tyrosinase," Journal of Korean Medical Institute of Dermatology & Aesthetics, 2005, pp. 91-97, vol. 1, No. 1.
Hee-Juhn Park, et al., "Syringin 4-O-beta-Glucoside, a New Phenylpropanoid Glycoside, and Costunolide, a Nitric Oxide Synthase Inhibitor, from the Stem Bark of *Magnolia sieboldii*," J. Nat. Prod., 1996, pp. 1128-1130, vol. 59, No. 12.
M. A. Kelm, et al., "A Brief Summary of Biologically Active Compounds from *Magnolia* spp.," Studies in Natural Products Chemistry, 2000, pp. 845-873, vol. 24, Elsevier Science B.V.
Soon Sung Lim, et al., "Effect of the Essential Oil from the Flowers of *Magnolia sieboldii* on the Lipopolysaccharide-Induced Production of Nitric Oxide and Prostaglandin E2 by Rat Peritoneal Macrophages," Planta Med, 2002, pp. 459-462, vol. 68.
Kazuo Watanabe, et al., "Introduction—The Genus *Magnolia*," Chapter 1, *Magnolia*—The genus *Magnolia*, 2002, Taylor and Frances.
Hyun-Kyung Lee, et al., "Anti-*Helicobacter pylori* Activity of Methanol Extracts from Korean Native Plant Species in Jeju Island," Agric. Chem. Biotechnol., 2004, pp. 91-96, vol. 47, No. 2.
"Methanol," 2011, The Merck Index online.
Sung-Hee Park, et al., "Costunolide, a Sesquiterpene from the Stem Bark of *Magnolia seiboldii*, Inhibits the RAS-Farnesyl-Proteintransferase," Abstract, Planta Med, 2001, pp. 358-359, vol. 67.
M. A. Kelm, et al., "Mosquitocidal Compounds from *Magnolia salicifolia*," International Journal of Pharmacognosy, Apr. 1997, pp. 84-90, vol. 35, No. 2, Taylor and Francis Ltd.
International Search Report—PCT/KR2007/006123 dated Aug. 21, 2008.

*Primary Examiner* — Brian-Yong S Kwon
*Assistant Examiner* — Jennifer Berrios
(74) *Attorney, Agent, or Firm* — Cantor Colburn LLP

(57) ABSTRACT

Disclosed herein is a skin-whitening cosmetic composition containing an extract of *Magnolia sieboldii* as an active ingredient. The *Magnolia sieboldii* extract has an excellent effect of inhibiting tyrosinase activity and melanin production, and the cosmetic composition containing the *Magnolia sieboldii* extract as an active ingredient has an excellent skin-whitening effect.

4 Claims, No Drawings

COSMETIC COMPOSITION FOR SKIN WHITENING COMPRISING THE EXTRACT OF *MAGNOLIA SIEBOLDII* AS ACTIVE INGREDIENT

TECHNICAL FIELD

The present invention relates to a skin-whitening cosmetic composition containing an extract of *Magnolia sieboldii* as an active ingredient.

BACKGROUND ART

The pigment of human skin or hair functions to protect the skin or hair from the deleterious effects of sunlight, particularly UV light. Persons lacking this pigment are very sensitive to sunlight, so that they are more likely to get burned. Also, there is a high likelihood of occurrence of skin cancer, even at young ages. It is known that short-wavelength UV rays (290-320 nm) and carcinogenic substances form harmful radicals, for example, oxygen radicals, on the skin, and such oxygen radicals attack skin cells to cause skin aging. The main function of melanin is to scavenge such harmful radicals, thus protecting the skin from damage caused by such harmful radicals. Accordingly, people having plenty of melanin have an effective defense system capable of protecting the skin from physical or chemical toxic substances. Factors promoting the production of melanin include, in addition to sunlight (UV light), estrogens and prostaglandins. Melanin is produced by melanocytes after the conversion of tyrosine to dopachrome through the action of the enzyme tyrosinase, followed by complex oxidation and condensation reactions. The produced melanin are transferred into skin cells and lost with epidermal peeling. This melanin production process is a naturally occurring phenomenon, and in a normal human skin, the overproduction of melanin does not occur. However, when the skin responds to external stimuli, for example, UV light, environmental pollutants or stresses, the overproduction of melanin will occur. When the overproduced melanin remains in the skin without being discharged out of the skin, pigmentation will occur. Among the above-described external stimuli, UV light is the greatest source stimulating melanin biosynthesis and can influence various processes associated with melanin production. That is, UV light acts as an important factor which induces the overproduction of melanin by promoting the activity of melanocytes, the secretion of hormones stimulating melanin biosynthesis, the oxidation of melanin, or the activity of tyrosinase.

The greatest characteristic of this melanin production mechanism is that only one enzyme, tyrosinase, is involved in the melanin production mechanism. When the tyrosinase activity is inhibited to prevent the production of melanin, a skin-whitening effect can be expected.

In the prior art, it is known to use ascorbic acid as a whitening substance (Japanese Patent Laid-Open Publication No. Hei 4-9320). However, ascorbic acid has a problem in that the activity thereof decreases with the passage of time, because the phase stability thereof in a formulation is poor. For this reason, various methods of stabilizing ascorbic acid with capsules or liposomes have recently been suggested, but a reliable stabilization method has not yet been suggested.

Also, it is known to use hydroquinone as another whitening substance (Japanese Patent Laid-Open Publication No. Hei 6-192062). Hydroquinone has excellent effects, but the use thereof in cosmetic products has been limited, because it is a carcinogenic substance.

Moreover, it is known to use kojic acid as still another whitening substance (Japanese Patent Laid-Open Publication No. Sho 56-7710). Kojic acid shows an excellent whitening effect due to an excellent ability to inhibit tyrosinase, but it has a problem in terms of the stability thereof in a formulation and was recently reported to be a carcinogenic substance.

In addition, it is known to use arbutin as still another whitening substance (Japanese Patent Laid-Open Publication No. 4-9315). Arbutin can be extracted from bearberries growing in alpine belts or can be obtained through synthesis. Also, it has a proven ability to inhibit tyrosinase, like kojic acid. However, arbutin has a structure in which sugar binds to hydroquinone, and it has a problem in that, when it is applied in cosmetic products, the sugar is separated by skin enzymes, such that skin irritation is induced by the hydroquinone.

Various patents and scientific articles are referred to throughout the specification. The disclosure of the cited patents and scientific articles is incorporated herein by reference in its entirety, such that the general knowledge of the technical field to which the present invention pertains and the content of the present invention are more clearly explained.

SUMMARY OF THE INVENTION

The present inventors have investigated various skin physiological activities for natural plant components in order to improve skin pigmentation and, as a result, have found that, among natural plant extracts, an extract of *Magnolia sieboldii* has excellent effects of inhibiting tyrosinase activity and melanin production, causes no skin irritation and has a very excellent skin-whitening effect, thereby completing the present invention.

Accordingly, it is an object of the present invention to provide a skin-whitening cosmetic composition containing an extract of *Magnolia sieboldii* as an active ingredient.

Another object of the present invention is to provide a cosmetic method comprising applying to the human skin said cosmetic composition containing the *Magnolia sieboldii* extract.

Other objects and advantages of the present invention will become more apparent from the following detailed description and the appended claims.

The present invention provides a skin-whitening cosmetic composition containing an extract of *Magnolia sieboldii* as an active ingredient. The *Magnolia sieboldii* extract of the present invention has excellent effects of inhibiting tyrosinase activity and inhibiting the melanin synthesis of melanocytes, compared to those of the prior whitening components. Also, the inventive cosmetic composition containing the *Magnolia sieboldii* extract as an active ingredient has a very excellent skin-whitening effect.

DETAILED DESCRIPTION OF THE INVENTION

The present invention provides a skin-whitening cosmetic composition containing an extract of *Magnolia sieboldii* as an active ingredient.

*Magnolia sieboldii*, which is the active ingredient of the cosmetic composition of the present invention, is a deciduous small tree belonging to the Magnoliaceae family, and the *Magnolia sieboldii* extract is obtained from the flower of *Magnolia sieboldii*.

*Magnolia sieboldii* is about 7 meters in height, and the leaves thereof are alternate, long oval-shaped and glassy. The white large flowers thereof open downward in May and June, and the fruits thereof are ripe in September. It is an ornamental plant, grows in the valleys of mountains and is distributed in all parts of Korea except for Hamgyeongbuk-do, Japanese and China.

The *Magnolia sieboldii* extract that is used in the present invention can be obtained from the flower, leaf, branch and root of a *Magnolia sieboldii* tree, preferably the flower or branch of the tree, and more preferably the flower.

The *Magnolia sieboldii* extract of the present invention can be prepared according to any conventional method known in the art, under conditions of conventional temperature and pressure using a conventional solvent.

The *Magnolia sieboldii* extract that is the active ingredient of the inventive cosmetic composition is preferably obtained by extraction with an extraction solvent selected from the group consisting of water, an anhydrous or hydrous lower alcohol having 1-4 carbon atoms, acetone, ethyl acetate, butyl acetate and 1,3-butylene glycol, more preferably ethyl alcohol, butanol or methanol, and even more preferably, ethyl alcohol. Said methyl alcohol is preferably 70% ethyl alcohol. The amount of the extraction solvent is preferably 1-10 times, more preferably 5-8 times, and most preferably 6 times the dry weight of *Magnolia sieboldii*.

The *Magnolia sieboldii* extract of the present invention is prepared through a process comprising the steps of:

(a) adding to dry *Magnolia sieboldii* an extraction solvent selected from the group consisting of water, an anhydrous or hydrous lower alcohol having 1-4 carbon atoms, acetone, ethyl acetate, butyl acetate and 1,3-butylene glycol;

(b) extracting the solvent-added *Magnolia sieboldii* of step (a) by heating either at 40-100☐ for 3-20 hours or at 4-40° C. for 1-15 days;

(c) filtering the extract of step (b), aging the filtrate by allowing it to stand at 5-10° C. for 7-10 days, and then additionally filtering the aged filtrate; and (d) drying the filtrate of step (c) in a rotary vacuum evaporator.

When 1,3-butylene glycol is used as the extraction solvent, the loss of dry weight is adjusted to 1% (w/w) after carrying out the extraction step (b), because it is difficult to dry the filtrate using the rotary vacuum evaporator.

Meanwhile, the scope of the *Magnolia sieboldii* extract of the present invention includes not only the extract obtained through the above-described extraction method, but also an extract obtained through a conventional purification process. It is understood that fractions obtained through various additional purification methods, for example, separation with an ultrafiltration membrane having a given molecular weight cut-off, separation by various chromatography systems (manufactured for separation according to size, charge, hydrophobicity or affinity), are included in the scope of the *Magnolia sieboldii* extract of the present invention.

The *Magnolia sieboldii* extract of the present invention can be prepared in the form of powder through an additional process, such as vacuum distillation, freezing drying or spray drying.

The *Magnolia sieboldii* extract of the present invention can exhibit the effect thereof by locally applying or spraying it on the skin. Thus, according to one embodiment of the present invention, the composition of the present invention can be prepared in the form of cosmetic compositions, including cream, lotion and skin lotion.

According to a preferred embodiment of the present invention, the content of the *Magnolia sieboldii* extract of the present invention is 0.00001-30.0 wt %, and preferably 0.0001-20.0 wt %, based on the total weight of the skin-whitening cosmetic composition. If the content of the *Magnolia sieboldii* extract is less than 0.00001 wt %, the effect thereof is difficult to show, and if it is more than 30 wt %, it has a high possibility of inducing skin irritation and can also have a great effect on the stabilization of a formulation. In a preferred embodiment of the present invention, a cosmetic composition containing 2.0 wt % of the *Magnolia sieboldii* extract was prepared and applied directly on the skin, and as result, it was observed that it had an excellent skin-whitening effect.

Also, the skin-whitening cosmetic composition of the present invention contains, in addition to the *Magnolia sieboldii* extract as an active ingredient, components which are conventionally used in cosmetic compositions, for example, conventional additives, such as an antioxidant, a stabilizer, a solubilizing agent, vitamins, a pigment and perfume, and carrier components.

The cosmetic composition of the present invention can be prepared in any formulation, which is conventionally prepared in the art. For example, it can be formulated into solution, suspension, emulsion, paste, gel, cream, lotion, powder, soap, surfactant-containing cleansing oil, powder foundation, emulsion foundation, wax foundation and spray, but the scope of the present invention is not limited thereto. More specifically, it can be prepared in the form of skin lotion, milk lotion, nourishing cream, massage cream, essence, eye cream, cleansing cream, cleansing foam, cleansing water, pack, spray or powder.

If the formulation of the present invention is paste, cream or gel, it may contain, as carrier components, animal oil, vegetable oil, wax, paraffin, starch, tragacanth, cellulose derivatives, polyethylene glycol, silicone, bentonite, silica, talc or zinc oxide.

If the formulation of the present invention is powder or spray, it may contain, as carrier components, lactose, talc, silica, aluminum hydroxide, calcium silicate or polyamide powder. Particularly, if it is spray, it may additionally contain a propellant, such as chlorofluorohydrocarbon, propane/butane or dimethyl ether.

If the formulation of the present invention is solution or emulsion, it may contain, as carrier components, a solvent, a solubilizing agent or an emulsifying agent, for example, water, ethanol, isopropanol, ethyl carbonate, ethyl acetate, benzyl alcohol, benzyl benzoate, propylene glycol, 1,3-butyl glycol oil, glycerol fatty ester, polyethylene glycol or sorbitan fatty acid ester.

If the formulation of the present invention is suspension, it may contain, as carrier components, a liquid diluent, such as water, ethanol or propylene glycol, and a suspending agent, such as ethoxylated isostearyl alcohol, polyoxyethylene sorbitol ester, polyoxyethylene sorbitan ester, microcrystalline cellulose, aluminum metahydroxide, bentonite, agar-agar or tragacanth.

If the formulation of the present invention is a surfactant-containing cleansing oil, it may contain, as carrier components, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester.

In another aspect, the present invention provides a cosmetic method comprising applying to the human skin the inventive cosmetic composition containing the *Magnolia sieboldii* extract.

The cosmetic method of the present invention includes all cosmetic methods comprising applying the inventive cosmetic composition to the human skin. That is, all methods known in the art, comprising applying the cosmetic composition to the skin, are included in the cosmetic method of the present invention.

The cosmetic composition of the present invention can be used alone or in combination with other cosmetic compositions. Also, the inventive cosmetic composition having an excellent skin-protecting effect can be used according to any conventional method, and the number of use thereof can vary depending on the skin condition or liking of a user.

If the cosmetic composition of the present invention is soap, a surfactant-containing cleansing formulation or a cleansing formulation containing no surfactant, it can be wiped, removed or washed with water, after it is applied to the skin. Concrete examples of said soap include, but are not limited to, liquid soap, powder soap, solid soap and oil soap, examples of said surfactant-containing cleansing formulation include, but are not limited to, cleansing foam, cleansing water, cleansing towel and cleansing pack, and examples of said surfactant-not containing cleansing formulation include, but are not limited to, cleansing cream, cleansing water and cleansing gel.

When the inventive cosmetic method comprising applying to the human skin the inventive cosmetic composition containing the *Magnolia sieboldii* extract is carried out, an excellent skin-whitening effect can be obtained.

Hereinafter, the present invention will be described in further detail with reference to examples. It is to be understood, however, that these examples are illustrative only, and the scope of the present invention is not limited thereto.

Preparation Example 1

Preparation I of *Magnolia sieboldii* Extract 200 g of the flowers of *Magnolia sieboldii*, washed with purified water and dried, were added to 1.2 L of water and extracted by heating in an extractor, equipped with a cooling condenser, at 70-90° C. for 5 hours. Then, the extract was filtered through 300-mesh filter cloth, aged by allowing it to stand at 5-10° C. for 7-10 days, and then filtered through Whatman No. 5 filter paper. The filtrate was dried in a rotary vacuum evaporator at 65° C., thus obtaining a dry weight of 10.8 g.

Preparation Example 2

Preparation II of *Magnolia sieboldii* Extract 200 g of the flowers of *Magnolia sieboldii*, washed with purified water and dried, were added to 1.2 L of water, extracted at 15-35° C. for 5 days, filtered through 300-mesh filter cloth, and further filtered through Whatman No. 5 filter paper. Then, the filtrate was concentrated two-fold in a rotary vacuum evaporator. Then, 0.6 L of 100% ethanol was added to the concentrate, aged by allowing it to stand at 5-10° C. for 7-10 days, and then filtered through Whatman No. 5 filter paper. The filtrate was dried in a rotary vacuum evaporator at 65° C., thus obtaining a dry weight of 12.5 g.

Preparation Example 3

Preparation III of *Magnolia sieboldii* Extract 200 g of the flowers of *Magnolia sieboldii*, washed with purified water and dried, were added to 1.2 L of water, extracted at 4-40° C. for 5 days, filtered through 300-mesh filter cloth, aged by allowing it to stand at 5-10° C. for 7-10 days, and then filtered through Whatman No. 5 filter paper. The filtrate was dried in a rotary vacuum evaporator, thus obtaining a dry weight of 10.6 g.

Preparation Examples 4-21

Preparation IV of *Magnolia sieboldii* Extract 200 g of the flowers of *Magnolia sieboldii*, washed with purified water and dried, were added to 1.2 L of each of the extraction solvents shown in Table 1 below and was extracted in the same manner as in Preparation Example 3. The extraction results are shown in Table 1.

TABLE 1

| Preparation Examples | Extraction solvents | Dry weight of final extract(unit: g) |
|---|---|---|
| Preparation Example 4 | 10% ethanol | 12.9 |
| Preparation Example 5 | 20% ethanol | 13.3 |
| Preparation Example 6 | 30% ethanol | 14.2 |
| Preparation Example 7 | 40% ethanol | 13.5 |
| Preparation Example 8 | 50% ethanol | 13.6 |
| Preparation Example 9 | 60% ethanol | 14.7 |
| Preparation Example 10 | 70% ethanol | 15.8 |
| Preparation Example 11 | 80% ethanol | 14.5 |
| Preparation Example 12 | 90% ethanol | 13.6 |
| Preparation Example 13 | 100% ethanol | 12.1 |
| Preparation Example 14 | Methanol | 13.2 |
| Preparation Example 15 | n-propanol | 10.5 |
| Preparation Example 16 | Isopropanol | 10.6 |
| Preparation Example 17 | 2-butanol | 11.2 |
| Preparation Example 18 | Acetone | 10.2 |
| Preparation Example 19 | Chloroform | 10.5 |
| Preparation Example 20 | Ethyl acetate | 10.6 |
| Preparation Example 21 | Butyl acetate | 10.3 |

Preparation Example 22

Preparation V of *Magnolia sieboldii* Extract 200 g of the flowers of *Magnolia sieboldii*, washed with purified water and dried, were added to 1.2 L of 1,3-butylene glycol, extracted for 48 hours, filtered through 300-mesh filter cloth, aged by allowing it at 5-10° C. for 7-10 days, and then filtered through Whatman No. 5 filter paper. The extract was subjected to the loss of dry weight, thus obtaining a final concentration of 1% (w/v).

Preparation Example 23

Preparation VI of *Magnolia sieboldii* Extract 200 g of the flowers of *Magnolia sieboldii*, washed with purified water and dried, were added to 1.2 L of 10%, ethanol and extracted by heating in an extractor equipped with a cooling condenser for 5 hours. Then, the extract was filtered through 300-mesh filter cloth, aged by allowing it to stand at 5-10° C. for 7-10 days, and then filtered through Whatman No. 5 filter paper. The extract was dried in a rotary vacuum evaporator at 65° C., thus obtaining a dry weight of 13.8 g.

Preparation Example 24

Preparation VII of *Magnolia sieboldii* Extract 200 g of the flowers of *Magnolia sieboldii*, washed with purified water and dried, were added to 1.2 L of each of the extraction solvents shown in Table 2 below and was extracted in the same manner as in Example 23. The extraction results are shown in Table 2.

TABLE 2

| Preparation Examples | Extraction solvents | Dry weight of final extract(unit: g) |
|---|---|---|
| Preparation Example 4 | 10% ethanol | 12.9 |
| Preparation Example 5 | 20% ethanol | 13.3 |
| Preparation Example 6 | 30% ethanol | 14.2 |
| Preparation Example 7 | 40% ethanol | 13.5 |
| Preparation Example 8 | 50% ethanol | 13.6 |
| Preparation Example 9 | 60% ethanol | 14.7 |
| Preparation Example10 | 70% ethanol | 15.8 |
| Preparation Example 11 | 80% ethanol | 14.5 |
| Preparation Example 12 | 90% ethanol | 13.6 |
| Preparation Example 13 | 100% ethanol | 12.1 |
| Preparation Example 14 | Methanol | 13.2 |
| Preparation Example 15 | n-propanol | 10.5 |
| Preparation Example 16 | Isopropanol | 10.6 |
| Preparation Example 17 | 2-butanol | 11.2 |
| Preparation Example 18 | Acetone | 10.2 |
| Preparation Example 19 | Chloroform | 10.5 |
| Preparation Example 20 | Ethyl acetate | 10.6 |
| Preparation Example 21 | Butyl acetate | 10.3 |

Test Example 1

Tyrosinase Activity Inhibitory Effect of *Magnolia sieboldii* Extract

40 μl of a solution of tyrosine (Sigma, USA) in 1.5 mmol/l of sodium phosphate buffer (pH 6.8) was used as a substrate, and each of the *Magnolia sieboldii* extracts prepared in Preparation Examples 1-32 was diluted in 0.05 M sodium phosphate buffer (pH 6.8), thus preparing sample solutions. 240 μl of each of the sample solutions was added to 40 ul of tyrosine, 20 μl of tyrosinase (1500 U/ml; Sigma) was added to the solution. Then, the mixture solution was allowed to react at 37° C. for 15 minutes, and then measured for absorbance at 490 nm. Herein, a solution having no *Magnolia sieboldii* extract added thereto was used as a control group. The inhibitory rate of tyrosinase activity was calculated according to the following equation 1, and the calculation results are shown in Table 3 below:

$$\text{Tyrosinase activity inhibitory rate (\%)} = \{1 - \text{absorbance } (O.D.490) \text{ of comparative group/absorbance } (O.D.490) \text{ of control group}\} \times 100 \quad \text{[Math Figure 1]}$$

TABLE 3

Tyrosinase activity inhibitory effect of *Magnolia sieboldii* extract (test concentration: 100 μg/ml)

| Test substances | Tyrosinase activity inhibitory rate (%) |
|---|---|
| Preparation Example 1 | 45.8 |
| Preparation Example 2 | 50.6 |
| Preparation Example 3 | 52.6 |
| Preparation Example 4 | 54.2 |
| Preparation Example 5 | 55.8 |
| Preparation Example 6 | 50.3 |
| Preparation Example 7 | 48.5 |
| Preparation Example 8 | 49.6 |
| Preparation Example 9 | 50.2 |
| Preparation Example 10 | 51.3 |
| Preparation Example 11 | 52.2 |
| Preparation Example 12 | 50.3 |
| Preparation Example 13 | 52.5 |
| Preparation Example 14 | 56.3 |
| Preparation Example 15 | 58.5 |
| Preparation Example 16 | 51.2 |
| Preparation Example 17 | 52.5 |
| Preparation Example 18 | 56.3 |
| Preparation Example 19 | 54.5 |
| Preparation Example 20 | 58.2 |
| Preparation Example 21 | 53.2 |
| Preparation Example 22 | 54.2 |
| Preparation Example 23 | 50.2 |
| Preparation Example 24 | 55.6 |
| Preparation Example 25 | 52.3 |
| Preparation Example 26 | 50.3 |
| Preparation Example 27 | 55.6 |
| Preparation Example 28 | 54.3 |
| Preparation Example 29 | 58.5 |
| Preparation Example 30 | 58.8 |

TABLE 3-continued

Tyrosinase activity inhibitory effect of *Magnolia sieboldii* extract (test concentration: 100 μg/ml)

| Test substances | Tyrosinase activity inhibitory rate (%) |
|---|---|
| Preparation Example 31 | 59.9 |
| Preparation Example 32 | 60.3 |

As can be seen from the results in Table 3 above, the *Magnolia sieboldii* extract samples, obtained through various extraction methods, showed tyrosinase activity inhibitory effects. This suggests that the inventive composition containing the *Magnolia sieboldii* extract shows an excellent effect of inhibiting tyrosinase activity.

Test Example 2

Melanin Production Inhibitory Effect of *Magnolia sieboldii* Extract (Melanin Analysis)

B-16 cells (mouse melanoma cells, Korea Cell Line Band) were inoculated onto a 12-well plate at a density of $10^4$ cells/well, and then cultured for one day. Each well of the plate was treated with varying concentrations of the *Magnolia sieboldii* extract and cultured for 3-4 days, and the culture medium in each well was centrifuged. The isolated cells were lysed with a solution of 500 μl of 1N NaOH in dimethylsulfoxide (DMSO) and heated in a water bath at 90° C. for 10 minutes. The lysed cells were centrifuged again, and the absorbance of the supernatant at 570 nm was measured. As a control group, cells untreated with the *Magnolia sieboldii* extract were used. The inhibitory rate of melanin production was calculated according to the following equation 2, and the calculation results are shown in Table 4 below:

Melanin production inhibitory rate (%)={1-absorbance (*O.D.*490) of comparative group/absorbance (*O.D.*) of control group}×100     [Math Figure 2]

TABLE 4

| Test substances | Melanin production inhibitory rate (%) |
|---|---|
| Preparation Example 1 | 66.8 |
| Preparation Example 2 | 65.7 |
| Preparation Example 3 | 65.3 |
| Preparation Example 4 | 64.3 |
| Preparation Example 5 | 66.7 |
| Preparation Example 6 | 67.3 |
| Preparation Example 7 | 68.6 |
| Preparation Example 8 | 66.7 |
| Preparation Example 9 | 65.3 |
| Preparation Example 10 | 66.3 |
| Preparation Example 11 | 63.2 |
| Preparation Example 12 | 65.3 |
| Preparation Example 13 | 63.4 |
| Preparation Example 14 | 65.3 |
| Preparation Example 15 | 68.5 |
| Preparation Example 16 | 63.2 |
| Preparation Example 17 | 63.6 |
| Preparation Example 18 | 65.2 |
| Preparation Example 19 | 68.3 |
| Preparation Example 20 | 67.5 |
| Preparation Example 21 | 65.3 |
| Preparation Example 22 | 65.3 |
| Preparation Example 23 | 66.3 |
| Preparation Example 24 | 65.5 |
| Preparation Example 25 | 63.3 |
| Preparation Example 26 | 65.2 |
| Preparation Example 27 | 64.2 |
| Preparation Example 28 | 68.3 |
| Preparation Example 29 | 68.5 |
| Preparation Example 30 | 68.7 |
| Preparation Example 31 | 69.8 |
| Preparation Example 32 | 67.3 |

As can be seen from the results in Table 4 above, it was confirmed that the *Magnolia sieboldii* extract had an excellent effect of inhibiting the melanin production of melanoma cells. Also, in each of the tests, no cytotoxicity was observed.

Hereinafter, formulation examples of the inventive cosmetic composition containing the *Magnolia sieboldii* extract as an active ingredient will be described in detail, but the inventive cosmetic composition is not limited to these formulation examples. Also, the *Magnolia sieboldii* extract used in the following formulation examples was a material obtained by dissolving the material of Preparation Example 10 in 30% 1,3-butylene glycol at a concentration of 1% (w/v).

Formulation Example 1

Skin Lotion

Among cosmetic compositions containing the *Magnolia sieboldii* extract, a skin lotion formulation is shown in Table 5 below.

TABLE 5

| Components | Contents (wt %) |
|---|---|
| *Magnolia sieboldii* extract | 2.0 |
| Glycerin | 5.0 |
| 1.3-butylene glycol | 3.0 |
| PEG 1500 | 1.0 |
| Allantoin | 0.1 |
| DL-pantenol | 0.3 |
| EDTA-2NA | 0.02 |
| Benzophenone-9 | 0.04 |
| Sodium hyaluronate | 5.0 |
| Ethanol | 10.0 |
| Octyl dodeses-16 | 0.2 |
| Polysorbate 20 | 0.2 |
| Preservative, perfume and pigment | q.s. |
| Distilled water | balance |
| Total | 100 |

Formulation Example 2

Astringent Lotion

Among cosmetic compositions comprising the *Magnolia sieboldii* extract, an astringent lotion formulation is shown in Table 6 below.

TABLE 6

| Components | Contents (wt %) |
|---|---|
| *Magnolia sieboldii* extract | 2.0 |
| Glycerin | 2.0 |
| 1.3-butylene glycol | 2.0 |
| Allantoin | 0.2 |
| DL-pantenol | 0.2 |
| EDTA-2Na | 0.02 |
| Benzophenone-9 | 0.04 |
| Sodium hyaluronate | 3.0 |
| Ethanol | 15.0 |
| Polysorbate 20 | 0.3 |
| Witch Hazel extract | 2.0 |
| Citric acid | q.s |
| Preservative, perfume and pigment | q.s |
| Distilled water | balance |
| Total | 100 |

Formulation Example 3

Milk Lotion

Among cosmetic compositions comprising the *Magnolia sieboldii* extract, a milk lotion formulation is shown in Table 7 below.

TABLE 7

| Components | Contents (wt %) |
|---|---|
| *Magnolia sieboldii* extract | 2.0 |
| Glyceryl stearate SE | 1.5 |
| Stearyl alcohol | 1.5 |
| Lanolin | 1.5 |
| Polysorbate 60 | 1.3 |
| Sorbitan stearate | 0.5 |
| Hydrogenated vegetable oil | 1.0 |
| Mineral oil | 5.0 |

TABLE 7-continued

| Components | Contents (wt %) |
|---|---|
| Squalane | 3.0 |
| Tiroctanoin | 2.0 |
| Dimethicone | 0.8 |
| Carboxyvinyl polymer | 0.5 |
| Glycerin | 0.12 |
| 1.3-butyleneglycol | 5.0 |
| Sodium hyaluronate | 3.0 |
| Triethanolamine | 0.12 |
| Preservative, perfume and pigment | q.s |
| Distilled water | balance |
| Total | 100 |

Formulation Example 4

Nourishing Cream

Among cosmetic compositions comprising the *Magnolia sieboldii* extract, a nourishing cream formulation is shown in Table 8 below.

TABLE 8

| Components (content: wt %) | Example 1 | Comparative Example 1 |
|---|---|---|
| *Magnolia sieboldii* extract | 2.0 | — |
| Lipophilic glycerin monostearate | 2.0 | 2.0 |
| Cetearyl alcohol | 2.2 | 2.2 |
| Stearic acid | 1.5 | 1.5 |
| Beewax | 1.0 | 1.0 |
| Polysorbate 60 | 1.5 | 1.5 |
| Sorbitan stearate | 0.6 | 0.6 |
| Hydrogenated vegetable oil | 1.0 | 1.0 |
| Squalane | 3.0 | 3.0 |
| Mineral oil | 5.0 | 5.0 |
| Trioctanoin | 5.0 | 5.0 |
| Dimethicone | 1.0 | 1.0 |
| Sodium magnesium silicate | 0.1 | 0.1 |
| Glycerin | 5.0 | 5.0 |
| Betaine | 3.0 | 3.0 |
| Triethanolamine | 1.0 | 1.0 |
| Sodium hyaluronate | 4.0 | 4.0 |
| Preservative, perfume and pigment | q.s. | q.s. |
| Distilled water | balance | balance |
| Total | 100 | 100 |

Formulation Example 5

Massage Cream

Among cosmetic compositions comprising the *Magnolia sieboldii* extract, a massage cream formulation is shown in Table 9 below.

TABLE 9

| Components | Contents (wt %) |
|---|---|
| *Magnolia sieboldii* extract | 2.0 |
| Lipophilic glycerin | 1.5 |

TABLE 9-continued

| Components | Contents (wt %) |
|---|---|
| monostearate | |
| Stearyl alcohol | 1.5 |
| Stearic acid | 1.0 |
| Polysorbate 60 | 1.5 |
| Sorbitan stearate | 0.6 |
| Isostearyl isostearate | 5.0 |
| Squalane | 5.0 |
| Mineral oil | 35.0 |
| Dimethicone | 0.5 |
| Hydroxyethylcellulose | 0.12 |
| Glycerin | 6.0 |
| Triethanolamine | 0.7 |
| Preservative, perfume and pigment | q.s |
| Distilled water | balance |
| Total | 100 |

Formulation Example 6

Essence

Among cosmetic compositions comprising the *Magnolia sieboldii* extract, an essence formulation is shown in Table 10 below.

TABLE 10

| Components | Contents (wt %) |
|---|---|
| *Magnolia sieboldii* extract | 2.0 |
| Glycerin | 10.0 |
| Betaine | 5.0 |
| PEG 1500 | 2.0 |
| Allantoin | 0.1 |
| DL-pantenol | 0.3 |
| EDTA-2Na | 0.02 |
| Benzophenone-9 | 0.04 |
| Hydroxyethylcellulose | 0.1 |
| Sodium hyaluronate | 8.0 |
| Carboxyvinyl polymer | 0.2 |
| Triethanolamine | 0.18 |
| Octyl dodecanol | 0.3 |
| Octyl dodeses-16 | 0.4 |
| Ethanol | 6.0 |
| Preservative, perfume and pigment | q.s. |
| Distilled water | balance |
| Total | 100 |

Formulation Example 7

Pack

Among cosmetic compositions comprising the *Magnolia sieboldii* extract, a pack formulation is shown in Table 11 below.

TABLE 11

| Components | Contents (wt %) |
|---|---|
| *Magnolia sieboldii* extract | 2.0 |
| Polyvinyl alcohol | 15.0 |
| Cellulose gum | 0.15 |
| Glycerin | 3.0 |
| PEG 1500 | 2.0 |
| Cyclodextrin | 0.15 |
| DL-pantenol | 0.4 |
| Allantoin | 0.1 |
| Ammonium glycyrrhizinate | 0.3 |
| Nicotinamide | 0.5 |
| Ethanol | 6.0 |
| PEG 40, hydrogenated castor oil | 0.3 |
| Preservative, perfume and pigment | q.s. |
| Distilled water | balance |
| Total | 100 |

Test Example 4

Test of Whitening Effect of Cosmetic Composition Containing *Magnolia sieboldii* Extract A test of the whitening effect of the inventive cosmetic composition containing the *Magnolia sieboldii* extract was carried out on twenty 19-40-year-old Korean women having a black skin. As measurement sites, three sites, each having an area of 1 cm$^2$, were marked on the arm of each of the test subjects. The two sites were applied with a cosmetic composition of Example 1, containing the *Magnolia sieboldii* extract and prepared according to the method of Formulation Example 4, and a cosmetic composition of Comparative Example 1, not containing the *Magnolia sieboldii* extract, respectively, and the remaining one site was used as a control group for comparison. Each of the cosmetic compositions was continuously applied for 8 weeks at an interval of 2 weeks, and after 8 weeks, the skin color (L value) was measured using Minolta CR 300. Then, the change in skin color (L) was calculated according to Equation 3, and the calculation results are shown in Table 12 below.

TABLE 12

| | Example 1 | Comparative Example 1 |
|---|---|---|
| ΔL value | 1.60 | 0.50 |

As can be seen in Table 12 which shows the change in skin color (L) after 8 weeks, the cosmetic formulation of Example 1, containing the *Magnolia sieboldii* extract, showed a high whitening effect. This suggests that the inventive cosmetic composition containing the *Magnolia sieboldii* extract has a very excellent whitening effect.

What is claimed is:

1. A method of using an extract of a flower of *Magnolia sieboldii* for whitening skin, the method comprising: administering to the skin of a person in need of whitening, a cosmetic composition comprising an effective amount of the extract of the flower of *Magnolia sieboldii* as an active ingredient to provide whitening, wherein the *Magnolia sieboldii* extract is present in an amount of 0.00001-30.0 wt. % based on the total weight of the cosmetic composition.

2. The method of claim 1, wherein the *Magnolia sieboldii* extract is present in an amount of 0.0001-20.0 wt % based on the total weight of the cosmetic composition.

3. The method of claim 1, wherein the *Magnolia sieboldii* extract is obtained by extraction with an extraction solvent selected from the group consisting of water, an anhydrous or hydrous lower alcohol having 1-4 carbon atoms, acetone, ethyl acetate and butyl acetate.

4. The method of claim 1, wherein the cosmetic composition is a formulation selected from the group consisting of solution, suspension, emulsion, paste, gel, cream, lotion, powder, soap, surfactant-comprising cleansing formulation, oil, powder foundation, emulsion foundation, wax foundation and spray.

* * * * *